United States Patent [19]

Petersen et al.

[11] 4,215,091
[45] Jul. 29, 1980

[54] METHOD OF DETERMINING THE MASS OF LIQUIDS

[75] Inventors: Otto Petersen, Krefeld; Franz Kersten, Toenisvorst, both of Fed. Rep. of Germany

[73] Assignee: Bayer Aktiengesellschaft, Leverkusen, Fed. Rep. of Germany

[21] Appl. No.: 891,103

[22] Filed: Mar. 28, 1978

[30] Foreign Application Priority Data

Apr. 14, 1977 [DE] Fed. Rep. of Germany ....... 2716468

[51] Int. Cl.² ............................................. G01N 31/16
[52] U.S. Cl. ................................................. 422/75
[58] Field of Search ..................... 73/299; 177/208; 23/253 R; 422/75

[56] References Cited

U.S. PATENT DOCUMENTS

| 2,604,383 | 7/1952 | Morse | 23/253 R |
| 2,627,453 | 2/1953 | Sheen | 23/253 R |
| 3,073,682 | 1/1963 | Lindsley | 23/253 R |
| 3,157,471 | 11/1964 | Harrison | 23/253 R |
| 3,693,738 | 9/1972 | Andrews | 73/299 |

Primary Examiner—Anthony V. Ciarlante
Attorney, Agent, or Firm—Sprung, Felfe, Horn, Lynch & Kramer

[57] ABSTRACT

A calibrated precision tube with an inlet and an outlet, and having a pressure transmitter at the bottom, is used for determining the mass of liquids.

4 Claims, 2 Drawing Figures

METHOD OF DETERMINING THE MASS OF LIQUIDS

This invention relates to a method of determining the mass of liquids.

In the factory and in the laboratory it is usual to determine the mass of a liquid formed or used by measuring its volume. The use of a titrating solution during titration is a classic example of this. The volume of liquid used is determined by means of a burette and the desired concentration is found by considering the concentration of the titrating solution. Since a "mass titration" is usually desired (the result is given as x g of the desired substance in 100 g of solution), calculations must be made and the analyses have a greater margin of error owing to the temperature variations than that which would be expected from measurements with a burette, having regard to its accuracy. Liquid dosing is also usually carried out nowadays according to the volume. The accuracy of known volumetric dosing pumps is at best 1%. When the dose is changed it is very difficult to reconstruct known apparatus.

The invention relates to a method of and an apparatus for determining the mass of liquids which may be used both in the factory and in the laboratory.

According to the invention, there is provided a method of determining the mass of a liquid, wherein the mass is determined from the difference between two pressure measurements in a calibrated precision tube. The invention also provides an apparatus for determining the mass of a liquid, comprising a calibrated precision tube having an inlet and an outlet and a pressure transmitter located at the bottom of the calibrated precision tube. The invention allows a high degree of accuracy in measurement and is flexible for adaption to various functions. In particular, it is adapted for automation.

The use of precision tubes and pressure transmitters affords substantial advantages. The mass of the liquid is measured with a high degree of accuracy. The measuring apparatus may be integrated in an installation and readily automated. Automatic measurement is considerably faster than manual visual measurement in a burette, and reading errors, which often occur, are avoided, as are the necessary calculations.

The calibrated precision tubes used in the invention may be, for example, KPG tubes made by the Schott company of Mainz, Federal Republic of Germany. They are available in various lengths and diameters and a wide range of measurements can therefore be covered. If the measuring purpose is changed, it is simple to reconstruct the apparatus according to the invention since the precision tube may be removed and replaced by axial manipulation, the tube being sealed with O-rings.

The choice of pressure transmitter depends upon the density and the filling height of the liquid. In a preferred embodiment, the precision pressure transmitter installed at the bottom of the precision tube converts the pressure measurement from the range of from 0 to 20 mbar into a range of from 0.2 to 1 bar. These pressure values are translated into electrical values by another transducer. With this apparatus, it is simple to install the pressure-current transducer and the control unit outside hazardous locations so that the apparatus may also be used in hazardous locations.

The mass liquid which has run off is provided directly from the difference between the measured values of the base pressure stored in the control unit before and after removing liquid. During titration, this value may be calculated directly by analysis. Similarly, the liquid mass released during a process may be determined when it is fed into the precision tube of the apparatus. It is also feasible to programme the control unit so that a feed and delivery valve are controlled in relation to the mass present in the precision tube, a typical case for dosing procedures.

The invention is illustrated in the accompanying drawings, in which.

Figure 1:
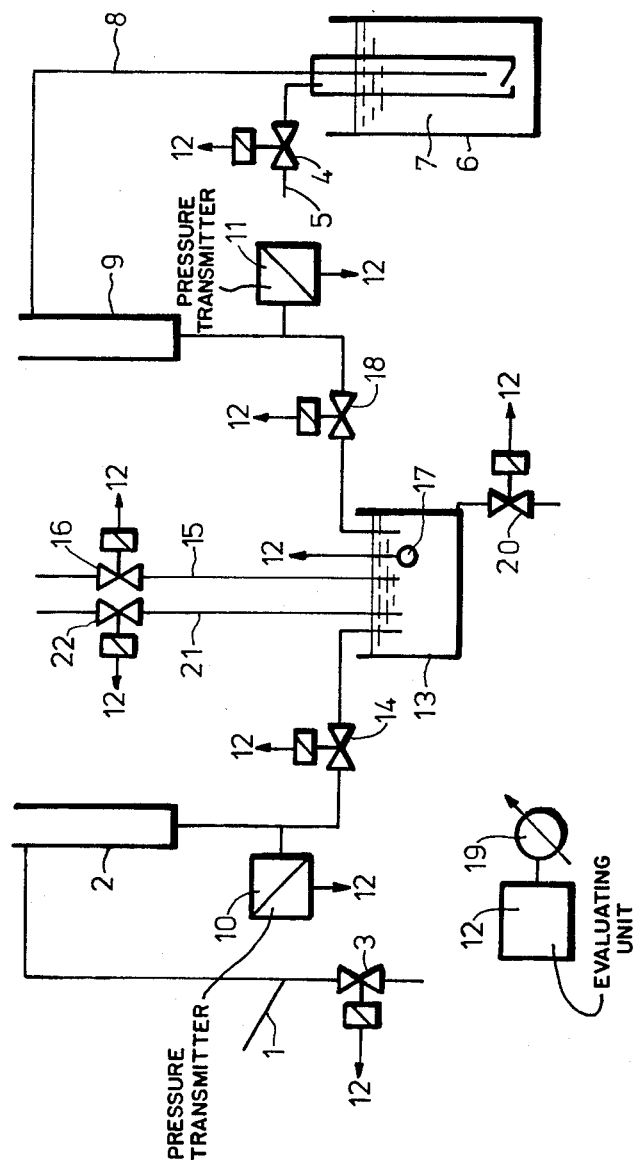
FIG. 1 shows an automatic titrating apparatus for industrial use.

Titrations are often carried out in the laboratory and in the factory for determining the concentration of one or more components in a solution. The component to be determined reacts with the titration solution. The end of this reaction must be detectable, for example by colour change, change in pH value or change in electrical conductivity. The consumption of titrating solution is proportional to the desired concentration. The automatic titration apparatus shown in FIG. 1 is particularly suitable for use in factories. Filling, emptying and cleaning is preferably carried out by means of pneumatically operated valves.

A solution whose concentration is to be determined advantageously flows via a levelling vessel (not shown) through a pipe 1. A valve 3 is closed so that the calibrated precision glass tube 2 is filled with the above mentioned solution. An alternative filling method is shown in relation to the filling of the calibrated precision glass tube which is filled with the titrating solution. Titrating solution 7 is conveyed from the supply container 6 via a pipe 8 into a calibrated precision glass tube 9 by opening a valve 4 in a pipe 5 which is filled with compressed air. Pressure transmitters 10 and 11 are installed at the bottoms of the calibrated precision glass tubes 2 and 9 respectively. The logic connections of the valves and measured value receivers to the control unit are not shown in the drawings; arrows with the reference numeral 12 are shown to indicate that the corresponding piece of apparatus is connected to the control and evaluating unit 12. It is to be understood that the filling process, for example, is stopped once the threshold values of the control unit are reached. The signals emitted by the pressure transmitters 10 and 11 are stored in the control and evaluating unit 12 after conversion into respective electrical signals.

Automatic titration for determining the concentration of a component in a solution takes place as follows.

A predetermined mass of solution to be measured is introduced into a titration vessel 13 via a valve 14. It may be necessary to dilute the solution and/or to add auxiliary agents. A pipe 15 which may be shut off via a valve 16 is provided for carrying out such auxiliary operations. The valve 16 in turn also communicates with the control and evaluation unit 12. In this example the apparatus for determining the final point of titration comprises an electrode 17 with which the pH value of the solution is measured. Based on the reading from the electrode 17 the titration solution 7 is introduced via a fine dosing valve 18 into the titration vessel 13. Upon reaching the end point of the reaction, the mass used in the calibrated precision glass tube 9 is determined by the control and evaluation unit 12 and the analysis value is displayed at 19.

After each analysis, the vessels 2 and 13 are emptied via a valve 20 and cleaned if necessary. In this example, a pipe 21 is provided for cleaning the titration vessel 13 and a valve 22 controlled by the control and evaluation unit 12 is installed in the pipe 21.

The apparatus described above is particularly suitable for use in factories. However, the apparatus according to the invention may also be used in the laboratory for many purposes. The automatic filling of the calibrated precision glass tube and clock times may frequently be dispensed with in laboratory apparatus. Even then, the mass titration, the substantial exclusion of operational errors in and the need for calculation, and the avoidance of reading errors remain as decisive advantages. Analysis may usually be carried out with this apparatus in a relatively short period by less qualified personnel.

It may be advantageous also to design supply and mixing vessels as calibrated precision glass tubes with pressure transmitters at the bottom and to feed the signals to an enlarged control unit so that operations before or after titration may also be automated.

Figure 2:
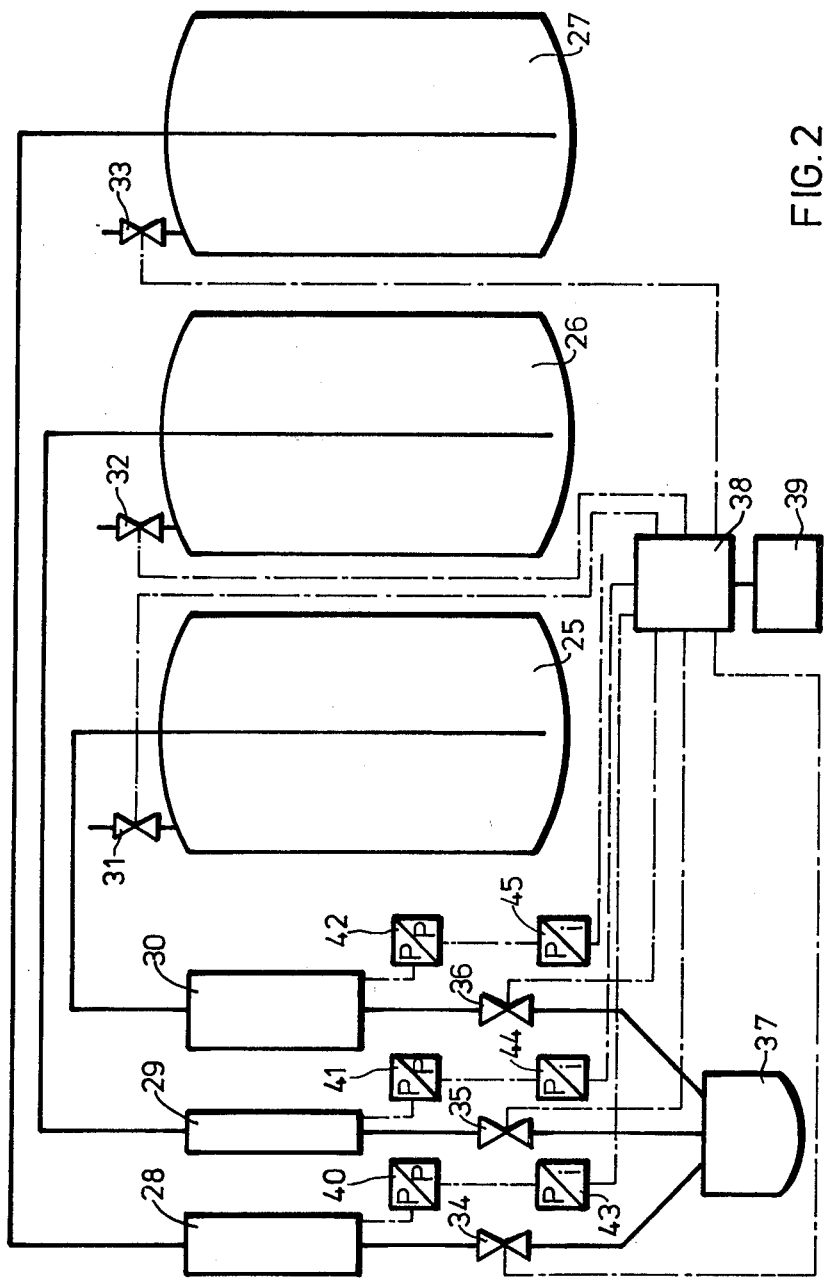
FIG. 2 shows a mixing apparatus.

FIG. 2 shows an automatically operating mixing apparatus. The object is to mix three liquids in a predetermined ratio. Three liquids in supply containers 25, 26 and 27 are conveyed into calibrated tubes 28, 29 and 30 by applying a pressure through valves 31, 32, 33.

A specific mixture of liquids is produced in the container 37 by periodically opening the valves 34, 35 and 36. The opening periods are determined by a central control unit 38, and the individual quantities are indicated digitally at 39. The ratio of the individual components is ensured to remain constant even with temperature variations by continuously measuring the liquid massed in the containers 28, 29, and 30. There are pressure transmitters 40, 41 and 42 at the bottom of the precision tubes 28, 29 and 30 which are followed by pressure/current transducers 43, 44 and 45. It is possible to determine the proportions from the vessel 37 to be emptied by means of the measuring methods described above and thus to automate the procedure further. The auxiliary and safety devices also required in the emptying units are not shown in the example.

What we claim is:

1. An apparatus for analyzing the concentration of a solution comprising: at least two calibrated precision tubes each having an inlet, an outlet and a precision pressure transmitter disposed at the bottom thereof, one tube receptive of a given amount of solution to be analyzed and the other tube receptive of a titration solution; a titration vessel including means for determining the point of titration therein; means coactive with the pressure transmitter in the one tube for introducing a predetermined mass of solution to be analyzed from the one tube into the titration vessel; and means for introducing titration solution from the other tube into the titration vessel until the point of titration is reached; whereby determination of the concentration of the solution to be analyzed is effected as a function of the output of the pressure transmitter in the other tube.

2. An apparatus according to claim 1, wherein the pressure transmitter comprises a transducer which develops an electric signal in response to changes in pressure.

3. An apparatus according to claim 1, adapted for use in a mixing apparatus comprising at least one calibrated precision tube fed from storage containers.

4. An apparatus according to claim 1, adapted for use as a laboratory titrating unit comprising a plurality of calibrated precision tubes in the form of storage containers for a solution to be tested and a titrating solution.

* * * * *